United States Patent [19]

Blanchard

[11] Patent Number: 5,621,990
[45] Date of Patent: Apr. 22, 1997

[54] KEEPSAKE HOLDER FOR BABY TEETH

[76] Inventor: Anastasia Blanchard, 760 Islip Ave., Brentwood, N.Y. 11717

[21] Appl. No.: 577,293

[22] Filed: Dec. 22, 1995

[51] Int. Cl.$^6$ ........................................... G09F 1/00
[52] U.S. Cl. ...................... 40/124.06; 40/124.2; 40/776; 206/83; 283/36; 283/117
[58] Field of Search .................... 40/124.1, 124.2, 40/537, 765, 776; 206/83, 232, 459.5; 283/36, 117

[56] References Cited

U.S. PATENT DOCUMENTS

| | | | |
|---|---|---|---|
| 1,029,526 | 6/1912 | Breezley, Jr. | 283/117 |
| 1,387,488 | 8/1921 | Helmer | 40/776 X |
| 1,388,947 | 8/1921 | Halpern et al. | 40/776 X |
| 1,780,878 | 11/1930 | Harris | 40/124.1 X |
| 1,978,925 | 10/1934 | Williams | 206/459.5 X |
| 3,144,932 | 8/1964 | Zerbo, Jr. | 206/459.5 X |
| 3,207,421 | 9/1965 | Hunger et al. | 206/459.5 X |
| 3,225,913 | 12/1965 | Lee | 206/232 X |
| 3,347,358 | 10/1967 | Meyers | 206/459.5 X |
| 3,435,868 | 4/1969 | Stermer | 206/232 X |
| 3,555,713 | 1/1971 | Leinbach | 40/776 X |
| 3,621,992 | 11/1971 | Osborne et a.l | 206/232 |
| 3,816,948 | 6/1974 | Mooney et al. | 40/776 X |
| 4,345,394 | 8/1982 | Sullivan | 40/124.2 X |
| 4,389,963 | 6/1983 | Pearson | 206/459.5 X |
| 4,694,956 | 9/1987 | Sims | 206/83 |
| 4,704,042 | 11/1987 | Eisen et al. | 40/776 X |
| 4,813,711 | 3/1989 | Bohlman | 283/36 X |
| 4,896,769 | 1/1990 | Merzon | 206/232 |
| 4,923,058 | 5/1990 | Dennison | 206/83 |
| 5,170,889 | 12/1992 | Cue | 206/459.5 X |
| 5,244,394 | 9/1993 | Serabian-Musto | 434/263 |
| 5,251,751 | 10/1993 | Prussen | 206/459.5 X |
| 5,303,819 | 4/1994 | Goldberg | 206/83 |
| 5,349,769 | 9/1994 | Okola | 40/124.1 |

Primary Examiner—Brian K. Green
Assistant Examiner—Andrea Chop
Attorney, Agent, or Firm—Galgano & Burke

[57] ABSTRACT

A keepsake holder for baby teeth which provides parents, guardians and others with a convenient way in which to save and display a child's baby teeth. The holder comprises a generally folded card having a top leaf and a bottom leaf. Attached to the inside of the top leaf are preferably graphical representations and dental terminology indicia corresponding to a child's twenty baby teeth. Attached to the bottom leaf is a plurality of date entry lines for entering the dates on the sheet that a child's baby teeth fall out. Also attached to the bottom leaf is a multi-pocketed double ply transparent sheet for separately retaining the child's baby teeth. Advantageously, cross-referencing indicia are disposed adjacent each graphical representation, dental terminology indicia, date entry line and pocket to cross-reference each retained baby tooth to its graphical representation, its dental terminology and the date that it fell out.

22 Claims, 2 Drawing Sheets

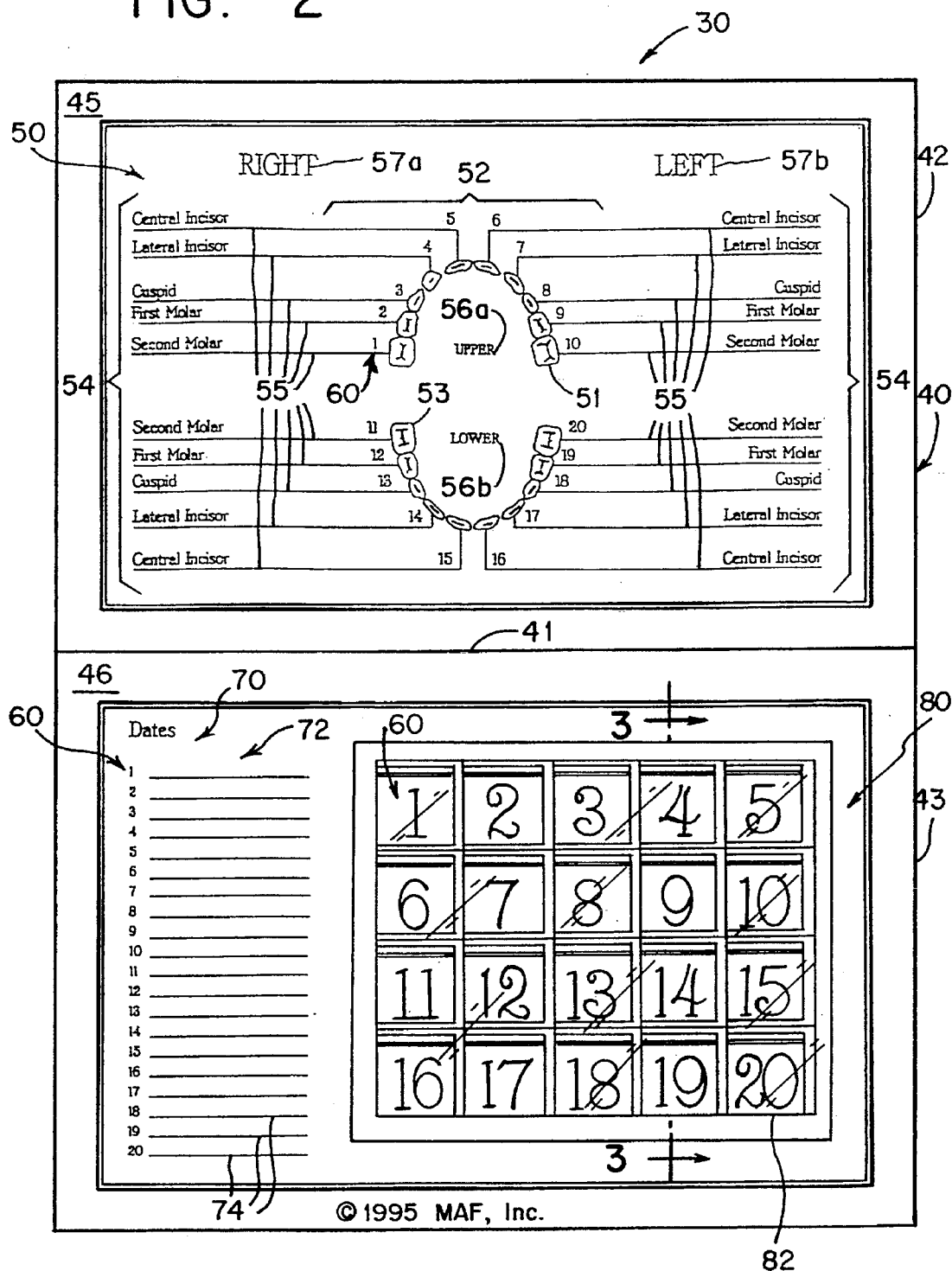

KEEPSAKE HOLDER FOR BABY TEETH

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates generally to keepsake holders for a child's baby teeth. More particularly, this invention relates to keepsake holders for identifying and attractively displaying a child's baby teeth.

Children have twenty baby teeth, ten in the top jaw and ten in the lower jaw. Children's baby teeth, after they have fallen out are often saved by the child's parents, guardian or others as a souvenir or memento of when the child was young. For example, a child's baby teeth are often saved in a jar, a small box, an envelope, or in a drawer of a desk or the like.

Thus, there is a need for a keepsake holder that enables a parent, a guardian or others to conveniently save a child's baby teeth as a souvenir or memento. In addition, there is a need for a keepsake holder that enables a parent or guardian to readily identify and attractively display a child's baby teeth after they have fallen out. Further, there is a need for a keepsake holder in which a parent or guardian can readily record in the holder the corresponding date that each baby tooth of a child falls out.

As far as is known, there is no presently available keepsake holder for baby teeth which provides identification of a child's twenty baby teeth, conveniently holds and attractively displays a child's baby teeth, and cross-references each of the baby teeth with its identification and with the date that it fell out.

SUMMARY OF THE INVENTION

Accordingly, it is an object of the present invention to provide a keepsake holder for baby teeth which is attractive for display at home on a table, shelf or desk.

It is also an object of the present invention to provide a keepsake holder for baby teeth in which the holder provides identification of a child's twenty baby teeth.

It is another object of the present invention to provide a keepsake holder for baby teeth in which the date that each of a child's twenty baby teeth falls out can be recorded in the holder.

It is yet another object of the present invention to provide a keepsake holder for baby teeth in which the holder separately and individually holds each of a child's twenty baby teeth.

It is a further object of the present invention to provide a keepsake holder for baby teeth in which the holder cross-references each baby tooth retained in the holder with its identification and the date that it fell out.

Certain of the foregoing and related objects are readily obtained in a keepsake holder for a child's baby teeth in which the holder comprises a generally planar support to which is attached identifying means for identifying each baby tooth of a child, recording means for recording the date that each baby tooth of the child falls out, and retaining means for separately retaining each baby tooth of the child. Further, cross-referencing indicia, operably disposed adjacent each of the identifying means, the recording means, and the retaining means, cross-reference each retained baby tooth to its identification in the identifying means and its recorded date in the recording means.

The identifying means preferably comprises graphical representations of each baby tooth of a child and dental terminology indicia of each baby tooth of a child. The recording means comprises a plurality of spaced apart date entry lines.

The retaining means preferably comprises a first ply and a second ply in which the plies are disposed in overlapping relationship and attached along a plurality of generally vertically extending seams and generally horizontally extending seams which intersect each other to form a plurality of pockets. Each pocket comprises a slit in the second ply adjacent its top edge defined by an adjacent horizontally extending seam so that a baby tooth of a child can be inserted and retained within the pocket. Preferably, the first ply and the second ply are fabricated from a polymeric material, and the vertically extending seams and the horizontally extending seams are attached by thermally bonding. Desirably, the second ply is fabricated from a clear or transparent material to permit visual observation and display of the baby teeth contained therein. Desirably the retaining means is suitably attached to the planar sheet with an adhesive material.

The cross-referencing indicia desirably include numerical indicia and preferably include the numbers from 1 through 20.

In a preferred embodiment of the present invention, the sheet comprises a top leaf and a bottom leaf and a fold line therebetween. The top leaf comprises a first front side and a first rear side, and the bottom leaf comprises a second rear side and a second front side. Desirably, the identifying means is disposed on the rear side of the top leaf and comprises graphical representations and dental terminology indicia of each baby tooth of a child. The recording means comprises a plurality of spaced apart date entry lines disposed on the front side of the bottom leaf, and the retaining means is also disposed on the front side of the bottom leaf and comprises a first ply and a second ply. The plies are disposed in overlapping relationship and attached along a plurality of generally vertically extending seams and generally horizontally extending seams which intersect each other to form a plurality of pockets.

BRIEF DESCRIPTION OF THE DRAWINGS

FIG. 2 is an enlarged plan view of the keepsake holder for baby teeth shown in FIG. 1, in which the keepsake holder is shown in an unfolded position.

DETAILED DESCRIPTION OF THE INVENTION

Figure 1:
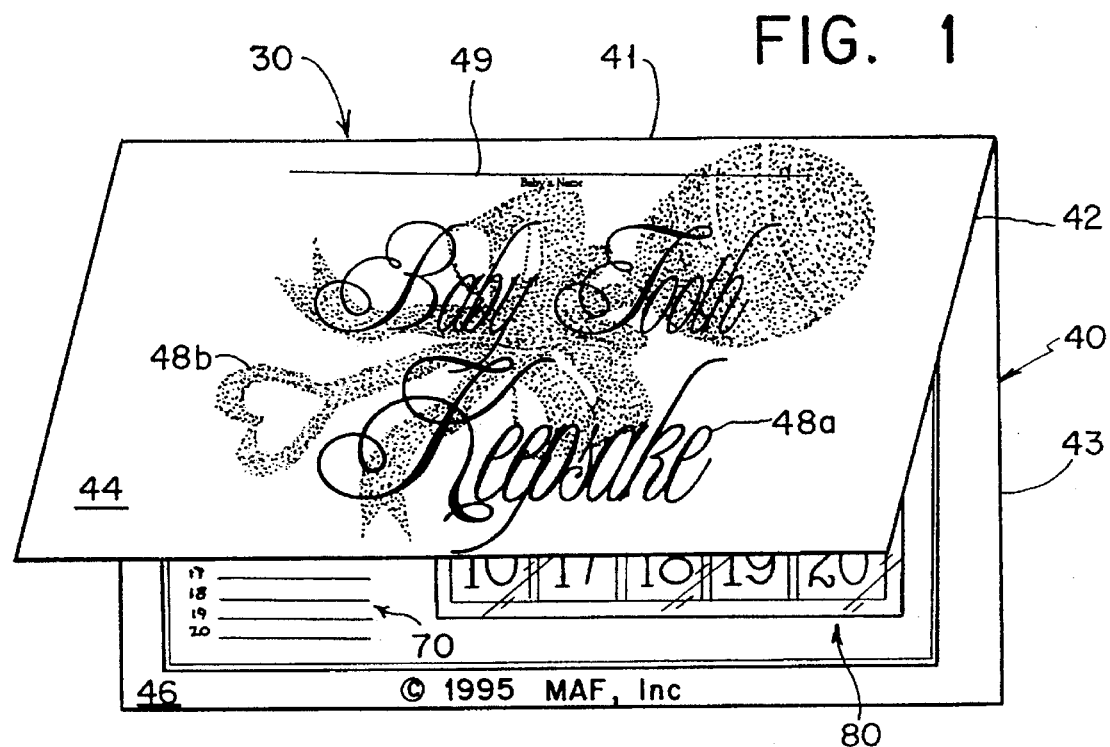
FIG. 1 is a perspective view of a keepsake holder for baby teeth according to the present invention in which the keepsake holder is shown in a folded position.

Turning now to FIGS. 1–2, therein illustrated is a keepsake holder 30 embodying the present invention in the form of a folded card for holding a child's baby teeth (not shown).

Holder 30 provides a parent or a guardian with a holder for conveniently saving a child's baby teeth in an organized arrangement which can be attractively displayed.

Holder 30 preferably comprises a single fold leaflet or sheet 40 having a top leaf 42 joined to a bottom leaf 43 via hinge line 41. Holder 30 further comprises identifying means 50 (FIG. 2) for identifying each baby tooth of a child, recording means 70 for recording in holder 30 the date that each baby tooth of the child falls out, and retaining means 80 for separately retaining and displaying each baby tooth of the child. Advantageously, cross-referencing indicia 60 relate each separately retained baby tooth of a child to its identification in identifying means 50 and its recorded date in recording means 70.

Figure 3:
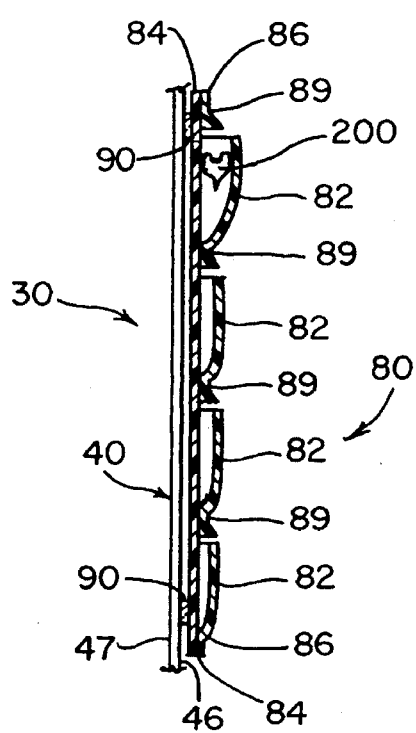
FIG. 3 is a cross-sectional view taken along line 3—3 of FIG. 2.

Referring again to FIGS. 1 and 2, top leaf 42 includes a front side 44 (FIG. 1) and a rear side 45 (FIG. 2), and bottom leaf 43 includes a front side 46 (FIG. 3) and rear side 47 (FIG. 3). When sheet 40 is placed in a folded position (FIG. 1), rear side 45 is disposed opposite front side 46. Front side 44 (FIG. 1) includes a "Baby Tooth Keepsake" label 48a, an illustration of a rattle 48b, and a name entry line 49 for entering a child's name, e.g., by writing or typing. Preferably, sheet 40 is fabricated from a substantially rigid and foldable material, e.g., a cardboard material, a laminated cardboard material, a plastic or polymeric material or the like. Desirably, label 48a, illustration 48b, and entry line 49 are colored pink for girls and blue for boys.

With reference to FIG. 2, identifying means 50 attaches to sheet 40, and specifically, to rear side 45 of top leaf 42. Preferably, identifying means 50 comprises graphical representations 52 of the top surface, i.e., crown, of each baby tooth of a child. The upper baby teeth of graphical representation 52 are portrayed in a downward U-shaped arch 51 which includes an "UPPER" label 56a below which are portrayed the lower baby teeth in an upward U-shaped arch 53 which includes a "LOWER" label 56b. One side of rear side 45 includes a "RIGHT" label 57a representing a child's baby teeth disposed on the right side of the child's mouth and the other side of rear side 45 includes a "LEFT" label 57b representing the child's baby teeth disposed on the left side of the child's mouth.

In addition, identifying means 50 also comprises dental terminology indicia 54 of a child's baby teeth. Specifically, each quadrant of rear side 45 is labeled with the following indicia; "Central Incisor," "Lateral Incisor," "Cuspid," "First Molar," and "Second Molar." A line 55 leads from each baby tooth represented in graphical representations 52 to its corresponding dental terminology indicia.

Referring still to FIG. 2, cross-referencing indicia 60 is operably disposed adjacent each identifying means 50, recording means 70 (described in greater detail below) and retaining means 80 (described in greater detail below) for cross-referencing each retained baby tooth in retaining means 80 to its identification in identifying means 50 and its recorded date in recording means 70. Specifically, cross-referencing indicia 60 comprise the numbers 1 through 20 with each number 1 through 20 disposed adjacent a different graphical representation 52 of each baby tooth. Although, cross-referencing indicia 60 are described in FIG. 2 as numbers, any suitable indicia could be used, e.g., letters, or symbols.

Recording means 70 attaches to sheet 40 for recording or entering on sheet 40 the date that each baby tooth of the child falls out. Specifically, recording means 70 is disposed and attached to the left side of front side 46 of bottom leaf 43 and comprises a suitable area 72 and a plurality of spaced apart date entry lines 74. Cross-referencing indicia 60 is operably disposed adjacent recording means 70 so that each number 1 through 20 is disposed adjacent a different date entry line 74.

Figure 4:
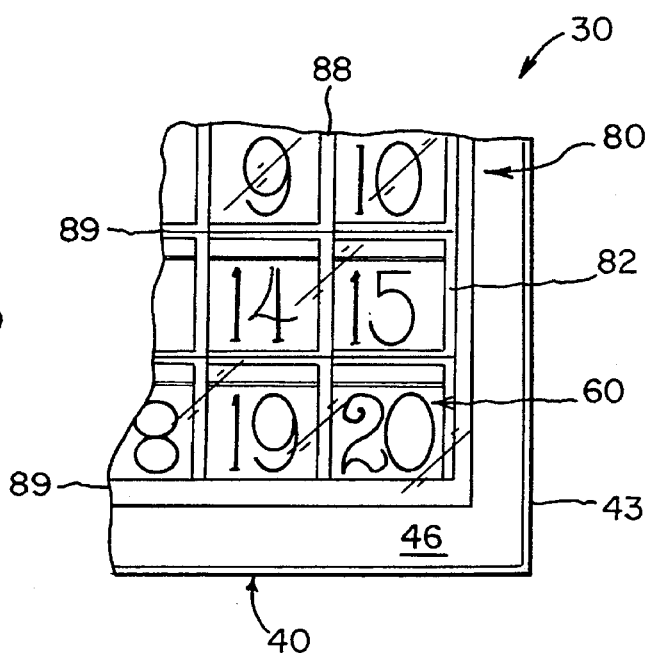
FIG. 4 is an enlarged, fragmentarily illustrated, partial plan view of the lower right corner of the keepsake holder for baby teeth shown in FIG. 1.

Referring now to FIGS. 2–4, retaining means 80 in the form of a multi-pocketed double ply transparent plastic sheet is adhesively attached to front side 46 of bottom leaf 43. Pockets 82 are arranged in five columns and four rows corresponding to a child's twenty baby teeth, numbered 1–20. A slit is provided in an outer ply of the double ply sheet adjacent a top edge of each pocket 82 to allow one to insert a baby tooth 200 (FIG. 3) in one of the pockets 82 and maintain it in a secure position therein.

As shown in greater detail in FIG. 3, retaining means 80 comprises a first generally rectangular ply 84 and a second generally rectangular ply 86. Ply 84 and ply 86 are disposed in overlapping relationship and are attached to each other along a plurality of vertically extending sections, or weld lines, or seams 88 (FIG. 4) and horizontally extending sections, weld lines, or seams 89 which intersect each other to form pockets 82. Each pocket 82 has a slit in ply 86 adjacent to its top edge defined by an adjacent horizontally extending seam 89 so that baby tooth 200 can be inserted and retained therein. Adhesive material 90 attaches retaining means 80 to sheet 40.

Preferably, ply 84 and ply 86 are fabricated from a plastic or polymeric material and vertically extending seams 88 and horizontally extending seams 89 are attached by thermal bonding. Desirably, ply 84 and ply 86 are fabricated from a clear or transparent plastic or polymeric material to permit visual observation and display of the baby teeth contained therein. In addition, cross-referencing means 60 is operably disposed on sheet 40 so that each number 1 through 20 is visible through a different pocket 82. It is appreciated that the ply adjacent sheet 40 need not be transparent but can be non-transparent or a solid color and cross-referencing means can be disposed on such ply and visible through the outermost ply.

For saving a child's baby teeth in holder 30, a parent or guardian would first identify a child's baby tooth that has fallen out using identifying means 50 to determine its corresponding number from cross-referencing indicia 60. The date that the baby tooth has fallen out is recorded adjacent the baby tooth's corresponding number in recording means 70 and the baby tooth is inserted into pocket 82 through which appears the baby tooth's corresponding number in retaining means 80. The same is repeated for each of the child's twenty baby teeth.

With reference again to FIG. 2, preferably, identifying means 50, recording means 70 and cross-referencing means 60 are printed directly onto sheet 40. It is also appreciated that identifying means 50, recording means 70 and cross-referencing means 60 can be a self adhesive label which attaches to sheet 40. It is further appreciated that the placements of identifying means 50, recording means 60 and retaining means 80 on sheet 40 can be suitably rearranged. Also, instead of the folded card or leaflet a single planar sheet would be equally suitable.

What is claimed is:

1. A keepsake holder for a child's baby teeth, said holder comprising:

a generally planar support;

identifying means attached to said planar support for identifying each baby tooth of a child, wherein said identifying means comprises at lest one of graphical representations of each baby tooth of a child and dental terminology indicia of each baby tooth of a child;

recording means attached to said planar support for recording the date that each baby tooth of the child falls out;

retaining means attached to said planar support for separately retaining each baby tooth of the child; and cross-referencing indicia comprising a first set of indicia, a second set of indicia, and a third set of indicia, said first set of indicia being operably disposed adjacent said identifying means, said second set of indicia being operably disposed adjacent said recording means, and said third set of indicia being operably disposed adjacent said retaining means, said cross-referencing indicia for cross-referencing each retained baby tooth in said retaining means to its identification in said identifying means and its recorded date in said recording means.

2. A keepsake holder according to claim 1, wherein said identifying means comprises graphical representations of each baby tooth of a child and dental terminology indicia of each baby tooth of a child.

3. A keepsake holder according to claim 1, wherein said recording means comprises a plurality of spaced apart date entry lines.

4. A keepsake holder according to claim 1, wherein said retaining means comprises a first ply and a second ply, said plies disposed in overlapping relationship and attached along a plurality of generally vertically extending seams and generally horizontally extending seams which intersect each other to form a plurality of pockets.

5. A keepsake holder according to claim 4, wherein each pocket comprises a slit in said second ply adjacent its top edge defined by an adjacent horizontally extending seam so that a baby tooth of a child can be inserted and retained within each pocket.

6. A keepsake holder according to claim 4, wherein said first ply and said second ply are fabricated from a polymeric material.

7. A keepsake holder according to claim 6, wherein said generally vertically extending seams and said generally horizontally extending seams are attached by thermally bonding.

8. A keepsake holder according to claim 4, wherein said second ply is fabricated from a transparent material to permit visual observation and display of the baby teeth contained therein.

9. A keepsake holder according to claim 4 wherein said retaining means is attached to said planar support with an adhesive material.

10. A keepsake holder according to claim 1, wherein said cross-referencing indicia comprise numerical indicia.

11. A keepsake holder according to claim 10, wherein said numerical indicia comprise the numbers from 1 through 20.

12. A keepsake holder according to claim 1 wherein said planar support comprises a top leaf and a bottom leaf and a fold line therebetween, said top leaf comprising a first front side and a first rear side, and said bottom leaf comprising a second rear side and a second front side.

13. A keepsake holder according to claim 12 wherein said identifying means is disposed on said first rear side of said top leaf and comprises at least one of graphical representations of each baby tooth of a child and dental terminology indicia of each baby tooth of a child.

14. A keepsake holder according to claim 12, wherein said identifying means is disposed on said first rear side of said top leaf and comprises graphical representations and dental terminology indicia of each baby tooth of a child.

15. A keepsake holder according to claim 12, wherein said recording means comprises a plurality of spaced apart date entry lines disposed on said second front side of said bottom leaf.

16. A keepsake holder according to claim 12, wherein said retaining means is disposed on said second front side of said bottom leaf and comprises a first ply and a second ply, said plies disposed in overlapping relationship and attached along a plurality of generally vertically extending seams and generally horizontally extending seams which intersect with each other to form a plurality of pockets.

17. A keepsake holder according to claim 16, wherein each pocket comprises a slit in said second ply adjacent its top edge defined by an adjacent horizontally extending seam so that a baby tooth of a child can be inserted and retained within each pocket.

18. A keepsake holder according to claim 16, wherein said plies are fabricated from a polymeric material.

19. A keepsake holder according to claim 18, wherein said generally vertically extending seams and said generally horizontally extending seams are attached by thermally bonding.

20. A keepsake holder according to claim 18, wherein said second ply is fabricated from a clear or transparent polymeric material to permit visual observation and display of the baby teeth contained therein.

21. A keepsake holder according to claim 12, wherein said cross-referencing indicia comprise numerical indicia.

22. A keepsake holder according to claim 21, wherein said numerical indicia comprise the numbers from 1 through 20.

* * * * *